United States Patent
Fichera et al.

(10) Patent No.: US 11,602,266 B2
(45) Date of Patent: Mar. 14, 2023

(54) FLEXIBLE ARTICULATING SURGICAL PROBE

(71) Applicant: Worcester Polytechnic Institute, Worcester, MA (US)

(72) Inventors: Loris Fichera, Worcester, MA (US); Kevin O'Brien, Worcester, MA (US); Zachary R. Boyer, Worcester, MA (US); Cory T. Brolliar, Worcester, MA (US); Benjamin G. Mart, Worcester, MA (US); Gregory S. Fischer, Boston, MA (US); Kenneth Stafford, Worcester, MA (US); Thomas Carroll, Worcester, MA (US); Karim A. Tarabein, Cleveland, OH (US)

(73) Assignee: Worcester Polytechnic Institute, Worcester, MA (US)

( * ) Notice: Subject to any disclaimer, the term of this patent is extended or adjusted under 35 U.S.C. 154(b) by 92 days.

(21) Appl. No.: 16/817,280

(22) Filed: Mar. 12, 2020

(65) Prior Publication Data
US 2020/0289201 A1    Sep. 17, 2020

Related U.S. Application Data

(60) Provisional application No. 62/818,356, filed on Mar. 14, 2019.

(51) Int. Cl.
*A61B 1/00*    (2006.01)
*A61B 1/05*    (2006.01)
(Continued)

(52) U.S. Cl.
CPC ............... *A61B 1/05* (2013.01); *A61B 1/008* (2013.01); *A61B 1/018* (2013.01); *A61B 1/06* (2013.01);
(Continued)

(58) Field of Classification Search
CPC ......... A61B 18/22; A61B 1/008; A61B 1/018; A61B 1/04; A61B 1/06;
(Continued)

(56) References Cited

U.S. PATENT DOCUMENTS 9,279,754 B1 * 3/2016 Arsenault, Jr. .......... G01N 3/08
2008/0287934 A1 * 11/2008 Hunter ................... A61B 18/20
606/10

(Continued)

OTHER PUBLICATIONS

International Search Report, PCT/US2020/022420, dated Jun. 25, 2020, pp. 2.

*Primary Examiner* — Timothy J Neal
*Assistant Examiner* — Sung Ham
(74) *Attorney, Agent, or Firm* — Armis IP Law, LLC

(57) ABSTRACT

An articulating, steerable surgical probe includes an elongated, flexible transfer tube adapted for insertion into a surgical region for endoscopic laryngeal laser surgery. A lumen is defined by an interior of the transfer tube, and a laser fiber extends through the lumen for delivering a therapeutic laser signal to a distal end of the laser fiber. An articulating tip at the distal end of the transfer tube is responsive to articulating forces from a retractable tether for directing the treatment probe in a direction of the articulation, and a linkage to the tether from a control module effects controlled retraction of the tether for articulating the tip towards a surgical target, such that the articulating tip imposing a bend radius based on a signal loss through the laser fiber.

17 Claims, 7 Drawing Sheets

(51) Int. Cl.
*A61B 18/22* (2006.01)
*A61B 1/008* (2006.01)
*A61B 1/018* (2006.01)
*A61B 1/06* (2006.01)
*A61B 18/00* (2006.01)
*A61B 17/00* (2006.01)

(52) U.S. Cl.
CPC .... *A61B 18/22* (2013.01); *A61B 2017/00309* (2013.01); *A61B 2017/00867* (2013.01); *A61B 2018/00327* (2013.01); *A61B 2018/00577* (2013.01)

(58) Field of Classification Search
CPC .......... A61B 2018/00327; A61B 2017/00867; A61B 2017/00309; A61B 2018/00577; A61B 5/4836; A61B 2018/2247; A61B 2018/2238; A61B 2018/00166; A61B 2017/0034; A61B 2018/00779; A61B 2018/00672; A61B 2018/00898; A61B 2017/00323; A61B 5/0059; A61B 2018/00982; A61B 2018/00196; A61B 2018/00202; A61B 1/0684; A61B 1/0676; A61B 1/05
USPC .................................................. 600/141, 142
See application file for complete search history.

(56) References Cited

U.S. PATENT DOCUMENTS

| | | | |
|---|---|---|---|
| 2009/0024085 A1 | 1/2009 | To et al. | |
| 2009/0137952 A1 | 5/2009 | Ramamurthy et al. | |
| 2012/0315001 A1* | 12/2012 | Beck | G02B 6/3861 156/293 |
| 2014/0046305 A1* | 2/2014 | Castro | A61B 34/70 606/1 |
| 2014/0194861 A1* | 7/2014 | Keeler | A61B 18/245 606/7 |
| 2014/0379000 A1* | 12/2014 | Romo | A61B 34/30 606/130 |
| 2015/0335227 A1* | 11/2015 | Jacobsen | A61B 1/00114 600/110 |
| 2016/0256226 A1* | 9/2016 | Castro | A61B 34/30 |
| 2016/0346513 A1* | 12/2016 | Swaney | A61B 17/3417 |
| 2019/0216294 A1* | 7/2019 | Matthison-Hansen | A61B 1/00135 |
| 2020/0100648 A1* | 4/2020 | Jensen | A61B 1/008 |
| 2021/0068899 A1* | 3/2021 | Nomura | G01M 11/31 |
| 2021/0085304 A1* | 3/2021 | Penny | A61B 34/71 |
| 2022/0142500 A1* | 5/2022 | Greenburg | A61B 1/2676 |

* cited by examiner

FLEXIBLE ARTICULATING SURGICAL PROBE

RELATED APPLICATIONS

This patent application claims the benefit under 35 U.S.C. § 119(e) of U.S. Provisional Patent App. No. 62/818,356, filed Mar. 14, 2019, entitled "FLEXIBLE ARTICULATING SURGICAL PROBE," incorporated herein by reference in entirety.

BACKGROUND

Laryngeal laser surgery is the standard of care for numerous benign and malignant pathologies of the larynx. A particular ailment is Recurrent Respiratory Papillomatosis (RRP). Affecting nearly 10,000 adults in the United States every year, RRP is characterized by the recurrent growth of multiple benign tumors inside the larynx, secondary to infection of the respiratory epithelium by human papillomavirus. Although benign, these tumors can aggressively spread through the entire respiratory tract and lead to a host of life-threatening complications, including obstruction of the airway, recurrent infections, and pneumonia. To date, no specific definitive treatment for RRP exists, and the disease is managed through repeated conventional endoscopic surgeries aimed to achieve disease control and prevent extensive tumor spreading. Once diagnosed, a typical RRP patient visits the operating room at least once a year, while more aggressive cases may require more than 4 surgeries per year.

SUMMARY

A miniaturized steerable laser probe assists access to anatomical locations within the human body that are beyond the reach of traditional instrumentation. The laser probe helps transform the surveillance and management of recurrent laryngeal disease from an operating-room-based paradigm to an office-based one. The steerable surgical probe includes an elongated, flexible transfer tube adapted for insertion into a surgical region. The transfer tube has a distal end and a proximate end, in which the proximate end is attached to a control module. An articulating tip is attached at the distal end of the transfer tube, and is responsive to articulating forces from a retractable tether. A linkage to the tether from the control module effects controlled retraction of the tether for articulating the tip towards a surgical target such as a growth or tumor for ablation. The control module also extends and rotates the transfer tube to allow the transfer tube to approach a surgical target, and the tether retracts to dispose the tip to articulate towards the surgical target.

Configurations herein are based, in part, on the observation that surgical operations in irregular internal regions, such as the throat and airway, present a cavitated area prone to obstructions and line-of-sight visibility constraints. Unfortunately, conventional approaches suffer from the shortcoming that conventional endoscopic instruments tend to be rigid, and can be difficult to intervene in surgical regions when tissue protrusions and recesses obscure the surgical field. Even with flexible endoscopes, a limited diameter of the endo scope restricts available surgical devices that may be employed. Accordingly, configurations herein substantially overcome the shortcomings of rigid and narrow endoscopes by providing a steerable, articulating laser probe adapted to fit within a 2 mm working channel of an endoscope for providing laser driven surgical intervention along with illumination and visual feedback provided by the endoscope.

A steerable tip may be articulated and rotated through a tube having notches cut along one side to permit flexure of a continuous side. The articulating tip has at least one notched void defining opposed sides of concentric sections, such that the opposed sides dispose towards each other and close the void in response to tethered retraction. The articulating tip may be formed from a nickel titanium tube having concentric notched sections partially removed to form an attachment between the sections. The nickel titanium tube may be partitioned into concentric sections by end milling or radial laser cutting, resulting in a tip with approximately 4 notched sections, although the number, width and depth of the notched sections may vary. The partially removed concentric sections form a substantially linear spine of continuous material parallel to an axis of the nickel titanium tube. The concentric sections remaining attached by the spine are pulled together as the spine deforms in response to the retracting tether.

In the example configuration, the transfer tube is adapted for passage through a working channel of an endoscopic surgical instrument, and allows flexible, steerable movement of the transfer tube and tip. A typical endoscopic instrument including the working channel has a diameter of 5 mm. The tether passes from the control module to the distal end through the transfer tube. The transfer tube includes coiled or braided polymer or plastic fibers reinforced with nitinol wire, and the transfer tube attaches to the tip via the nitinol wire welded to nitinol comprising the tip.

In further detail, the steerable surgical probe device as defined herein includes an elongated, flexible transfer tube adapted for insertion into a surgical region, such that the transfer tube has a distal end and a proximate end, and the proximate end attaches to a control module. A lumen is defined by an interior of the transfer tube, and a laser fiber extends through the lumen and is adapted for delivering a therapeutic laser signal to a treatment probe defined by a distal end of the laser fiber emanating from the distal end of the transfer tube. An articulating tip at the distal end of the transfer tube is responsive to articulating forces from a retractable tether for directing the treatment probe in a direction of the articulation, and a linkage to the tether from the control module effects controlled retraction of the tether for articulating the tip towards a surgical target, such that the articulating tip imposes a bend radius based on a signal loss through the laser fiber.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

The description below presents an example of the articulating probe operable with an endoscopic surgical tool for accessing a constrained surgical region. A particular usage includes laryngeal laser surgery is the standard of care for numerous benign and malignant pathologies of the larynx. While the disclosed novel laser probe could enhance treatment of many suitable clinical conditions, one where it would help in particular is Recurrent Respiratory Papillomatosis (RRP). Affecting nearly 10,000 adults in the United States every year, RRP is characterized by the recurrent growth of multiple benign tumors inside the larynx. The necessary conventional recurrent treatment is burdensome in time and cost.

Figure 1:
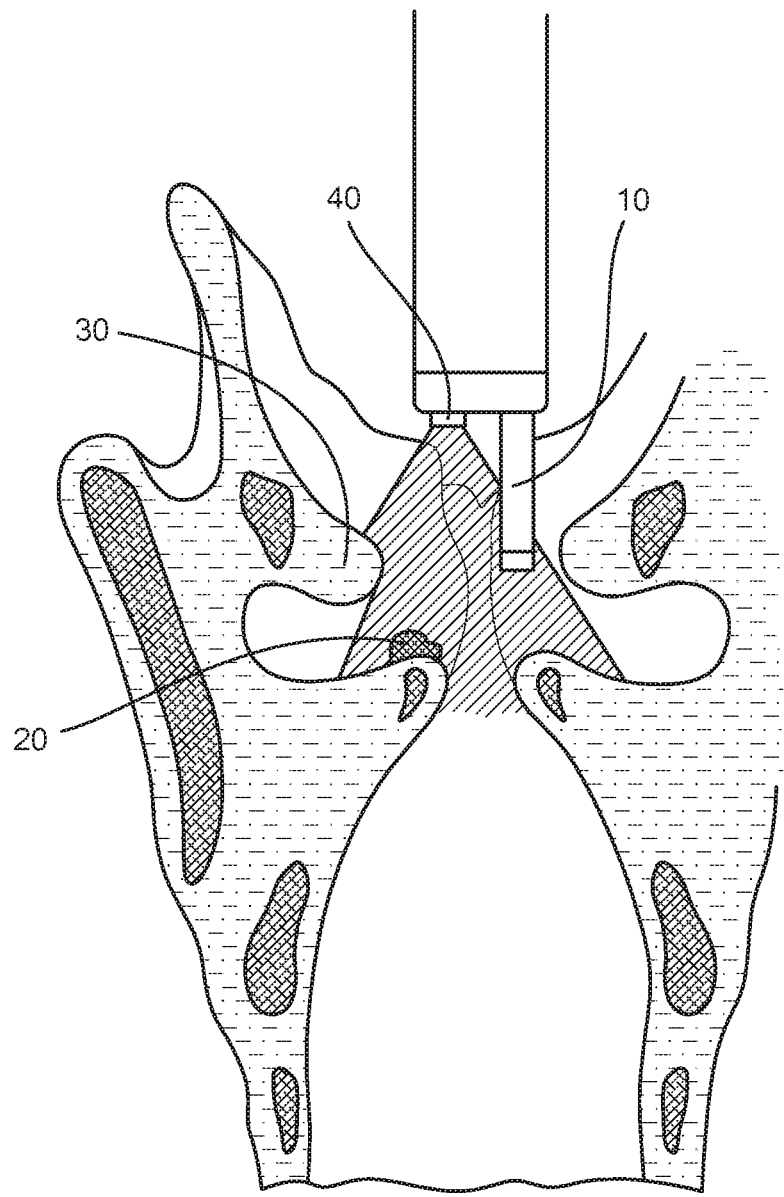
FIG. 1 is a context diagram showing a prior art endoscopic procedure on a throat cavity of a patient.

FIG. 1 is a context diagram showing a prior art endoscopic procedure on a throat cavity 50 of a patient. One way to cut the cost of care for RRP would be to replace the inpatient surgical procedures currently required to control the disease into outpatient procedures. Prior studies have verified the clinical viability of treating RRP endoscopically in an office context using lasers. Nonetheless, conventional thin laser probes 10 used in these procedures lack an articulation mechanism and therefore cannot treat lesions 20 that lie off the axis of the delivery fiber and/or are visible obscured by structures 30. Patients who present with disease in locations considered "unfavorable" within the larynx, i.e. locations that do not allow for a straight access path or in a line of sight of an endoscopic camera 40, are therefore ineligible for outpatient treatment and are referred for surgery in the operating room.

Figure 2A:
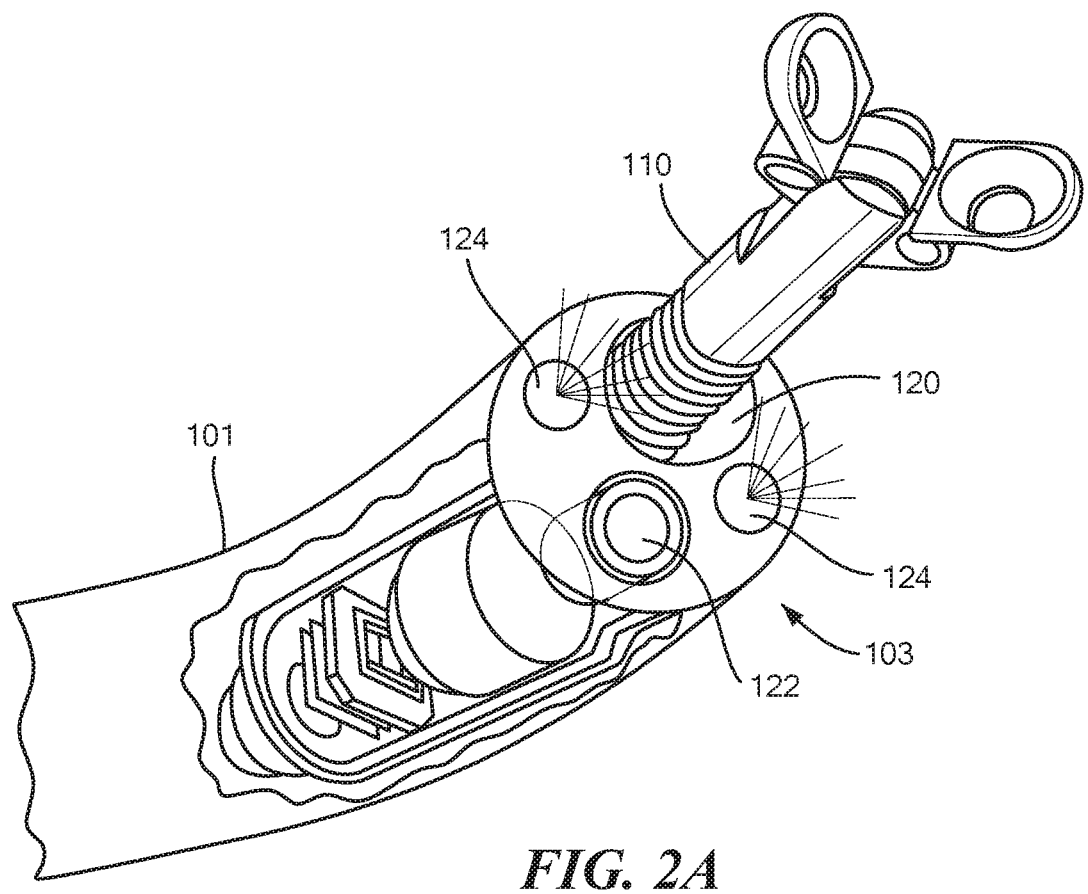
FIGS. 2A and 2B show an instrument channel in an endoscope suitable for use with configurations herein.
Figure 2B:
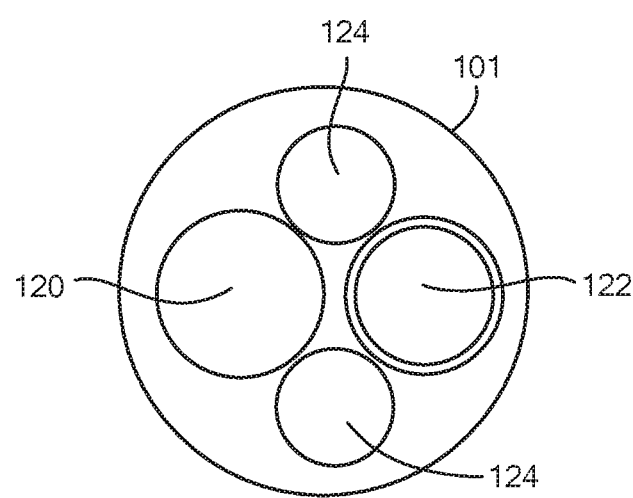

FIGS. 2A and 2B show an instrument channel in an endoscope suitable for use with configurations herein. Referring to FIG. 2A, an endoscope is one of a family of minimally invasive surgical tools that enter the body through a small incision, rather than a general opening to the surgical field. Sometimes referred to as "keyhole" types of procedures, the name varies according to the surgical target, such as laparoscopy (abdomen or pelvis), arthroscopy (knee and orthopedics) and colonoscopy (lower gastrointestinal). A common denominator is the use of a narrow instrument (often 5 mm or smaller in diameter) to pass surgical tools, illumination and visual aids through a small incision rather than a large general opening, facilitating recovery.

FIG. 2A shows an endoscope 101 suitable for use with configurations herein. A surgical tool 110 such as a forceps passes through a working channel 120 of the endoscope 101. Other channels or devices such as a camera 122 and LEDs 124 (Light Emitting Diodes) for illumination may also be included at the surgical end of the endoscope 101. As the flexible endoscope 101 often has a diameter of 5 mm or less, and the working channel 120 has a diameter of 2 mm or less, a challenge posed to surgical tools 110 is to fit within the 2 mm working channel 120 diameter, thus often restricting such tools 110 to a width of 1.8 mm.

FIG. 2B shows a cross section 130 of the endoscope 101 for use with the articulating probe as disclosed herein. Referring to FIGS. 2A and 2B, a flexible endoscope 101 has a working channel 120 receptive to an elongated instrument for passage therethrough. The flexible endoscope 101 has a therapeutic end 103 for accessing a surgical site. The elongated instrument such as the articulating tip disclosed herein extends beyond the therapeutic end 103 for access to the surgical site. The flexible endoscope 101 further includes a camera channel or camera 122 for visual image transmission and at least one illumination source 124 at the therapeutic end 103 for illuminating the surgical site following insertion. Configurations herein may dispose the articulating tip from either a rigid endoscope as in FIG. 1 or a flexible endoscope 101 as in FIGS. 2A and 2B, however greater mobility is afforded with the flexible endoscope 101.

Figure 3:
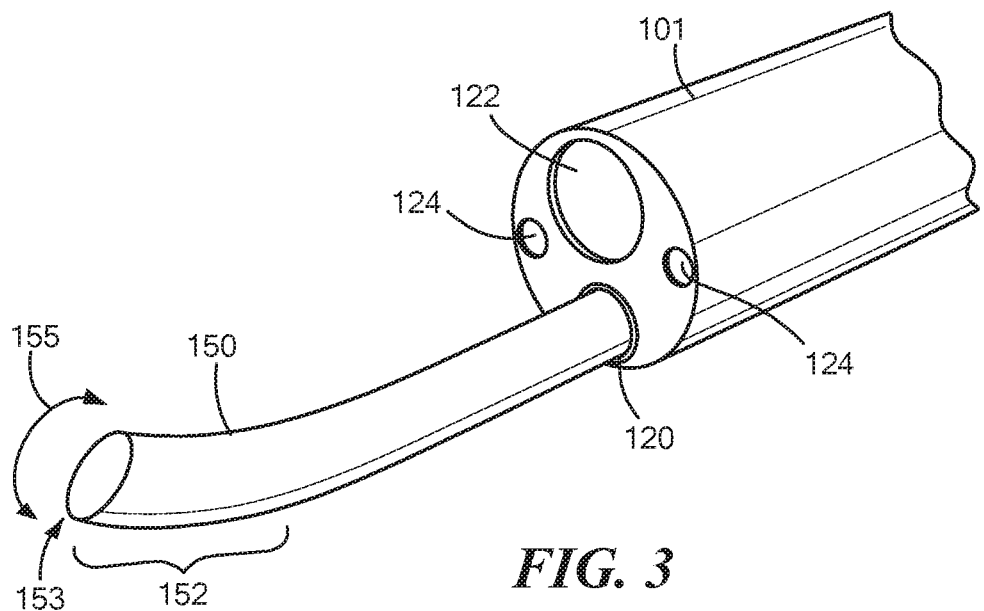
FIG. 3 shows an endoscope as in FIGS. 2A and 2B in operation with the articulating laser probe as disclosed herein.

FIG. 3 shows an endoscope as in FIGS. 2A and 2B in operation with an articulating laser probe 150 (laser probe) as disclosed herein. The laser probe 150 occupies the working channel 120 as with other surgical tools 110. An articulation region 152 is defined by an articulating tip of the laser probe, discussed further below. Steering is accomplished by rotation of the articulating tip as shown by arrows depicting arcuate path 155

Development of a steerable laser probe 150 at a scale consistent with laryngeal application as disclosed herein presents challenges as articulation mechanisms based on traditional linkages (e.g. ball/universal joints, cables and pulleys) can only be miniaturized to a certain extent. Rather, configurations herein employ miniaturized tube-like continuum bending mechanisms. Curved bending sections can be realized in the body of a thin tube via the creation of notches and the attachment of a pull-wire at the tip. Candidate tube materials include super-elastic Nickel-Titanium (NiTi), or Nitinol, and polyether ether ketone (PEEK). These bending mechanisms present two characteristics that make them particularly suited: they can be manufactured in small diameters (<2 mm), and they have a hollow lumen 153 (i.e. the inner diameter of the tube) which can be used to pass a laser fiber through.

Figure 4:
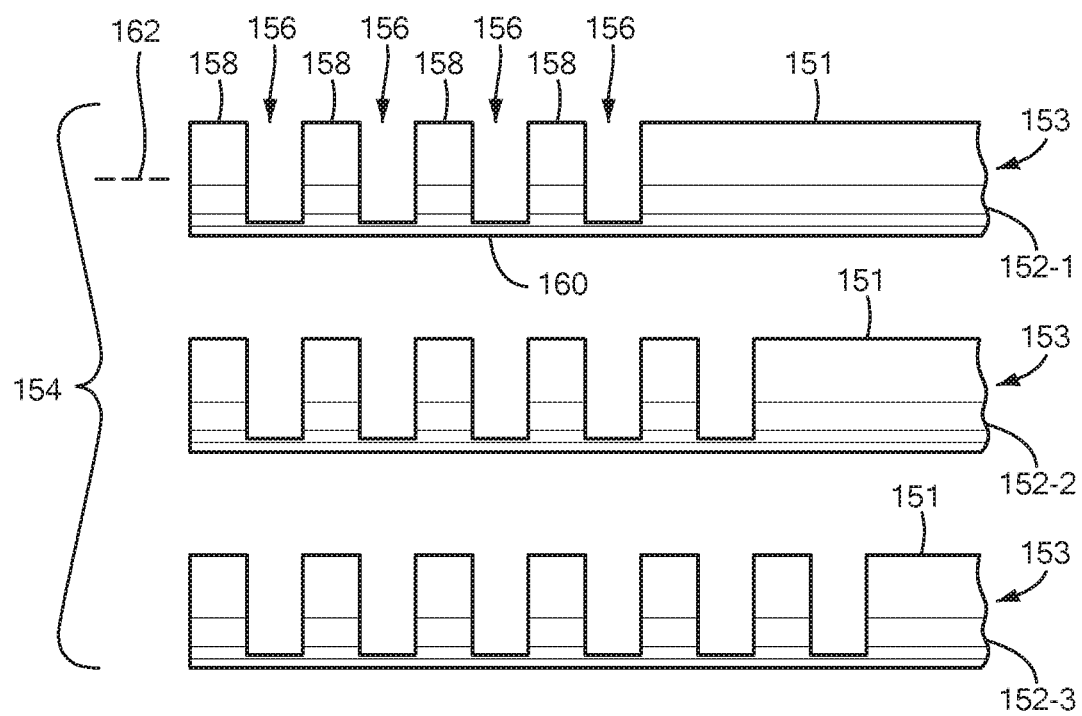
FIG. 4 shows the articulation mechanism in the articulating laser probe of FIG. 3.

FIG. 4 shows the articulation mechanism in the articulating laser probe of FIG. 3. Referring to FIG. 4, several example tip sections for use as the articulating region 152-1 . . . 152-3 (152 generally) are shown. An articulating tip 154 is formed from a nickel titanium (nitinol) transfer tube 151 having concentric notched sections, gaps or voids 156 partially removed to form an attachment between concentric sections 158 on each side flanking the void 156. The articulating tip 154 generally has at least one notched void 156 defining opposed concentric sides, such that the opposed concentric sides are adapted to dispose towards each other and close the void in response to tethered retraction.

Nitinol is a nonmagnetic alloy of titanium and nickel that after being deformed tends to return to its original shape. The partially removed concentric sections form a substantially linear spine 160 of continuous material parallel to an axis 162 of the nickel titanium tube. Various numbers of voids 156 may be implemented, such as 4 voids (152-1), 5 voids (152-2) and 6 voids (152-3).

Figure 5:
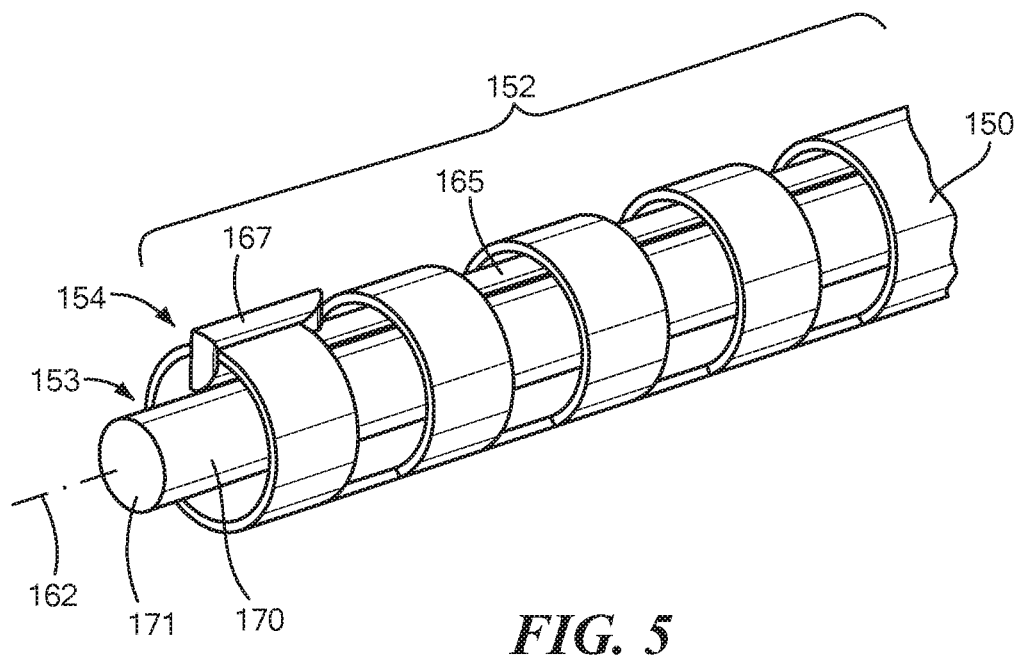
FIG. 5 shows the construction of the articulating laser probe using the mechanism of FIG. 4.

FIG. 5 shows the construction of the articulating laser probe 150 using the mechanism of FIG. 4. Referring to FIGS. 4 and 5, the transfer tube 151 housing a laser fiber 170 is adapted for passage through the working channel 120 of an endoscopic surgical instrument 101, generally following a path along the axis 162 through the lumen 153. The articulating tip 154 has an angle of articulation resulting in a bend radius and a maximum angle of articulation is based on a signal strength of a laser signal emanating from the laser probe following passage through an articulated fiber portion at the bend radius.

The example depicts a single articulating link defining the tip, actuated by retraction of a tether 165 anchored by an attachment 167 to one of the concentric sections 158. While it is theoretically possible to include an arbitrary number of articulated links, practical considerations of a control tether within the small confines effectively limits the approach to one or two links. With a flexible endoscopic surgical instrument 101, a single articulating tip suffices for substantially reaching laryngeal locations.

Figure 6:
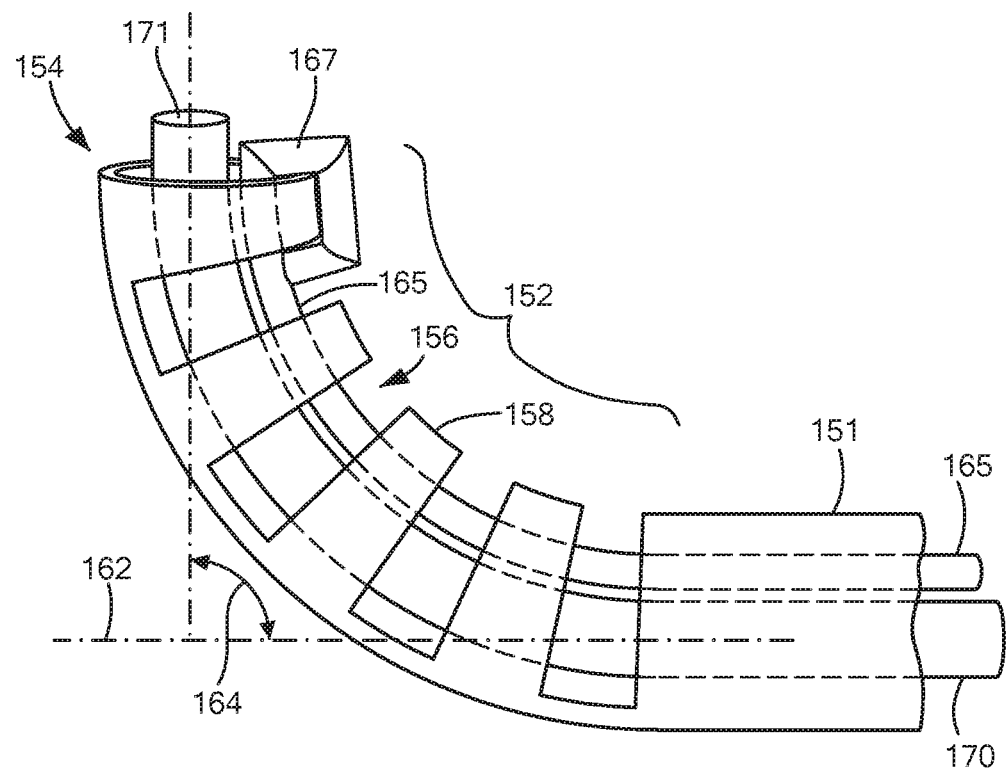
FIG. 6 show an articulated tip in the laser probe of FIG. 5.

FIG. 6 shows the articulating region 152 in the laser probe of FIG. 5. Referring to FIGS. 5 and 6, upon retraction of the tether 165 (controlled as discussed below in FIGS. 8A-8B), concentric sections 158 are drawn together, closing voids 156 between the sections and resulting in an articulation angle 164 by a deviation from a nominal axis 162 of the lumen 153. The tether 165 typically exhibits substantial strength and flexibility, such as a nitinol wire and an attachment 167 of suitable strength, such as a weld, loop or hook.

Figure 7:
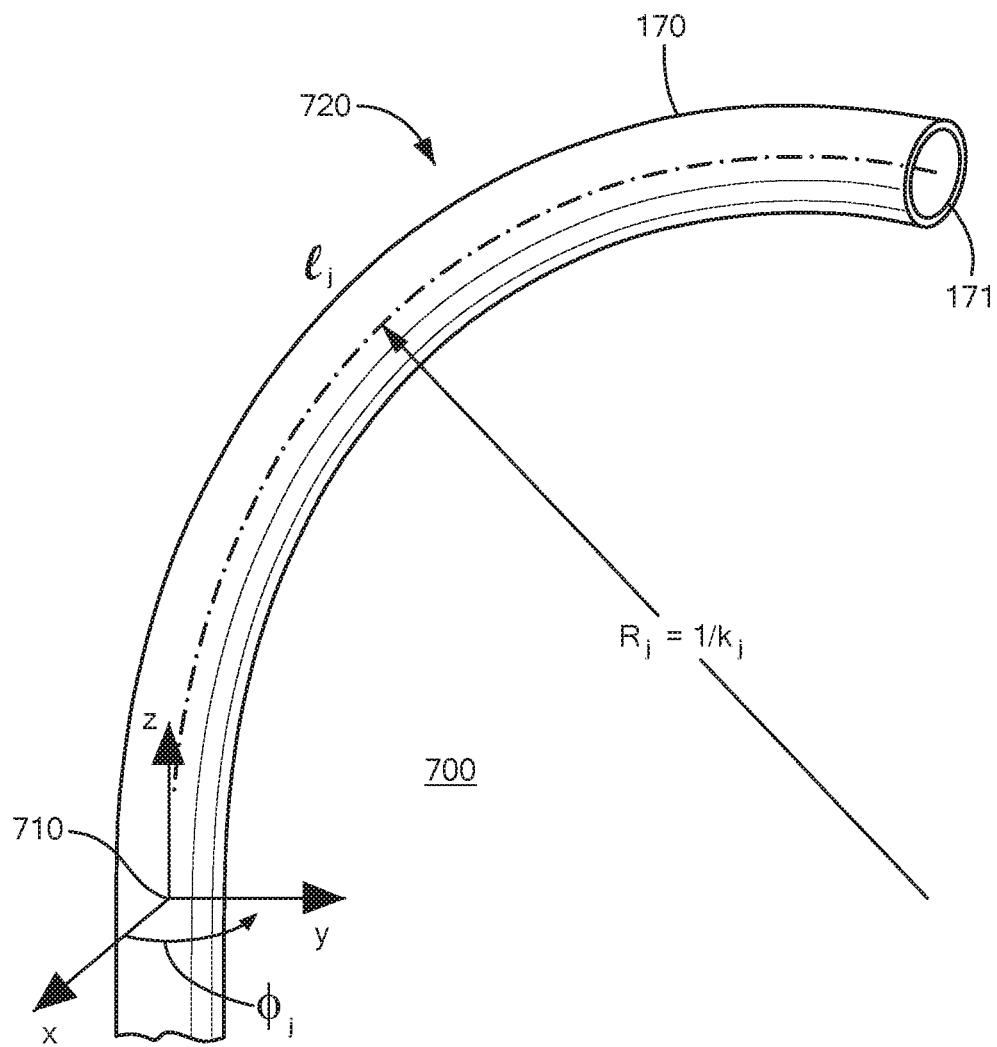
FIG. 7 shows bending kinematics for a laser fiber contained in the tip of FIG. 6.

FIG. 7 shows bending kinematics for a laser fiber contained in the tip of FIG. 6. Referring to FIGS. 6 and 7, upon deployment, the articulating region 152 and tip 154 occupy a volume 700 in an interior of the laryngeal or other surgical region. The 3 axes 710 defining this space impart a bend 720 to the laser fiber 170. Material and physical characteristics impose a signal degradation on the transported laser energy for delivery as laser emissions 171 from the therapeutic end 103 of the endoscope 101

To estimate the extent of volume that can be reached by a given articulating region 152, a Rapidly-expanding Random Tree (RRT) approach may be employed to generate a large number (10,000) of locations that can be reached in a collision-free path. RRT provides probabilistic completeness, meaning that the longer the approach is invoked, the more likely it is that it will cover the true reachable volume entirely. In our simulations, RRT operates on the arc parameters kj, f j and lj of each individual link, which are left to vary freely within defined boundaries. In a particular configuration, a MATLAB® boundary function may be used to calculate the tightest single-region boundary around the points generated by RRT, and to estimate its corresponding volume.

Figure 8A:
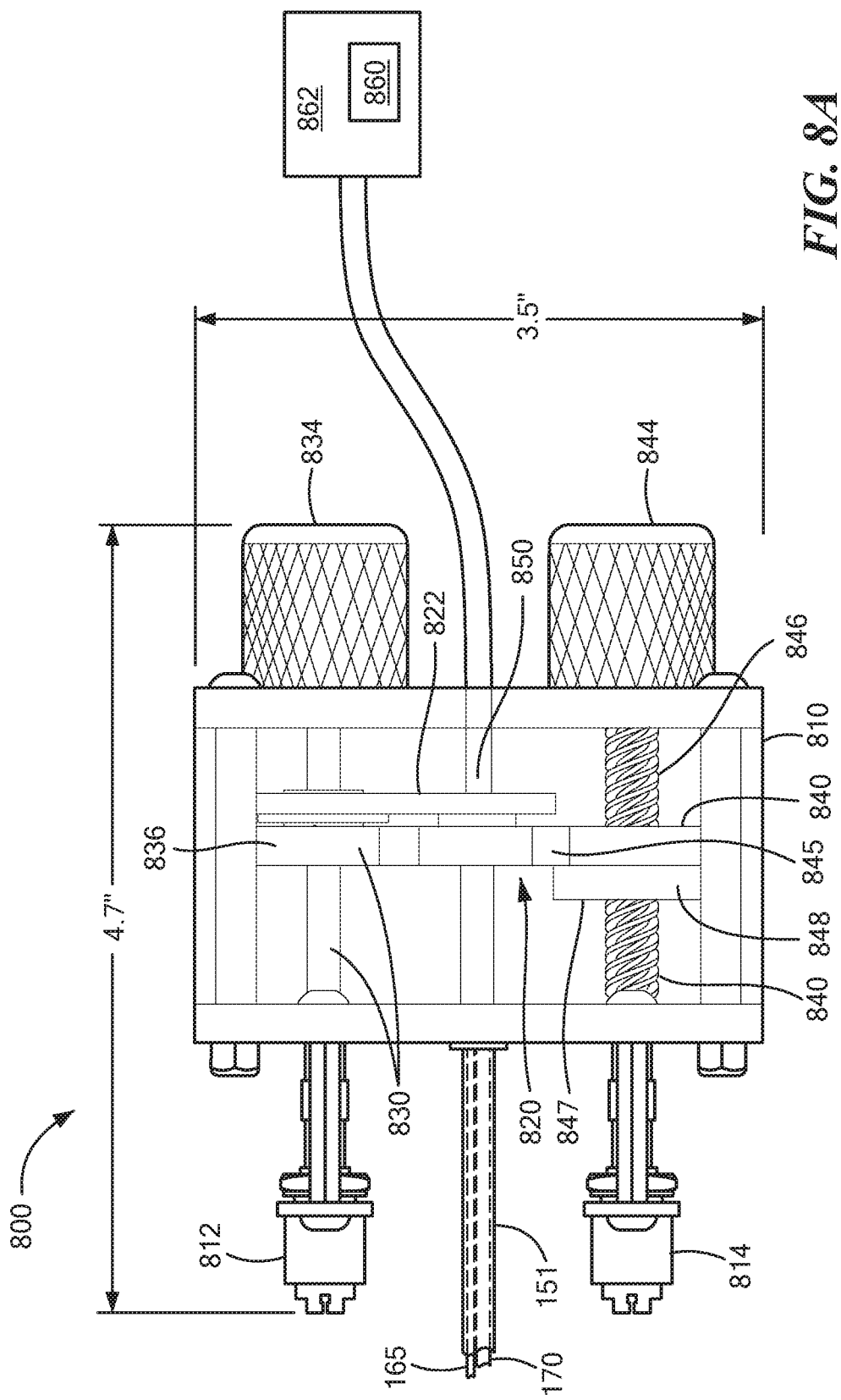
FIGS. 8A and 8B show a control module operable for articulating and steering the articulating laser probe of FIGS. 3-6.
Figure 8B:
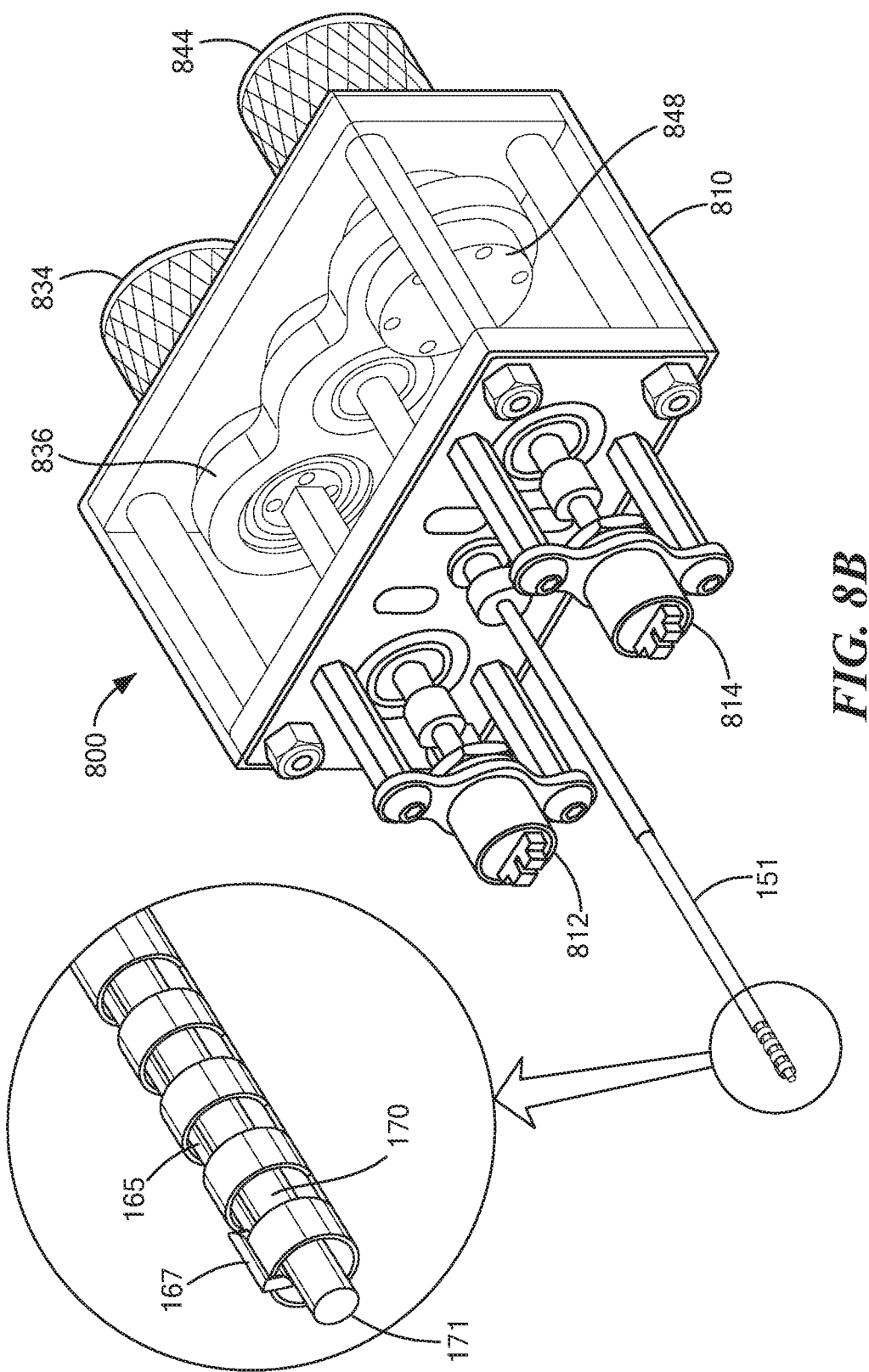

FIGS. 8A and 8B show a control module operable for articulating and steering the articulating laser probe of FIGS. 3-5. FIG. 6A shows a plan view of the control module. Referring to FIGS. 3-8B, a steerable surgical probe device 800 includes an elongated, flexible transfer tube 151 adapted for insertion into a surgical region. The transfer tube 151 has a distal end defined by the articulating tip 154 and a proximate end attached to a control module 810. The lumen 153 is defined by an interior of the transfer tube 151, and the laser fiber 170 extends through the lumen 153 and is adapted for delivering a therapeutic laser signal to a laser emission 171 defined by a distal end of the laser fiber 170 emanating from the distal end of the transfer tube 151.

The articulating tip 154 at the distal end of the transfer tube 151 is responsive to articulating forces from the retractable tether 165 for directing the laser probe 150 in a direction of the articulation. The linkage 167 to the tether 165 from the control module 810 effects controlled retraction of the tether for articulating the tip 154 towards a surgical target, such that the articulating tip 154 imposes a bend radius based on a signal loss through the laser fiber 170.

The control module 810 provides a control linkage 820 between the transfer tube 151 and the control module, including a steering control 830 operable to rotate the transfer tube 151 for transferring an axial rotation to the articulating tip 154, and an advancement control 840 for advancing the transfer tube 151 relative to the control module 810 for disposing the distal end relative to the control module. A retraction control 850 draws the retractable tether 165 in a direction towards the control module and articulating the tip. Rotary encoder 812 engages with the steering control 830 and is configured to transmit a signal indicative of rotation of the transfer tube 151. Rotary encoder 814 engages with the advancement control 840, and configured to transmit a signal indicative of advancement of the transfer tube 151 based on rotation of a threaded member 847. Rendering devices such as monitors provide a GUI (graphical user interface) for the encoder values as well as video from the camera 122.

A rotary steering control 830 in the control module 810 includes a rotating steering knob 834 and a rotary linkage 836 between the steering knob 834 and the transfer tube 151, such that the rotary linkage 836 provides circumferential rotation of the transfer tube 151 for disposing the tip 154 in an arcuate path 155 based on the articulation.

An advancement control 840 in the control module includes a rotating advancement knob 844 and a threaded rod 846 attached to the rotating advancement knob 844. An actuation plate 848 has a threaded receptacle 847 such that the threaded rod extends through the threaded receptacle. The threaded receptacle 847 is therefore responsive for advancement based on rotation of the threaded rod 846, and a linkage 845 between the threaded receptacle and the transfer tube 151 disposing the transfer tube. The retraction control allows bidirectional movement of the retractable tether 165 by disposing the retractable tether in a direction towards and away from the control module 810 for varying an angle of articulation of the tip 154.

FIG. 8B shows a perspective view of the control module engaged with the transfer tube 151 for performing a procedure with the articulating laser probe 150. Continuing to refer to FIGS. 3-8B, the control module 810 further includes a detection circuit 860 in conjunction with a laser drive circuit 862 driving the laser emissions 171 from the laser fiber 170. The detection circuit 860 is configured to identify a signal loss through the laser fiber 170 during articulation, as the bend in the fiber 170 tends to degrade a signal strength. The detection circuit 860 compares the identified signal loss to a threshold indicative of a signal falling below a minimal therapeutic effectiveness, such as when the laser emission 171 is degraded for ablating or removing afflicted tissue. The detection circuit 860 renders an indication of excessive signal degradation, either as a discrete warning or as a relative strength level allowing medical personnel to evaluate.

An articulation actuator 822 attaches to the retractable tether 165 (retractable tendon), such that the retractable tether 165 is coupled to the distal end of the transfer tube 151 on a distal side of one of the notched voids 156. The tether 165 is adapted to draw the opposed concentric sides of the sections 158 into proximity for inducing a deformable flexure in an unbroken circumference or spine 160 of the transfer tube 151 as discussed above with respect to FIG. 4.

In a particular configuration, the transfer tube 151 includes a nickel titanium tube forming the tip welded to the transfer tube 151, or the entire transfer tube is nickel titanium. The actuating tether 165 is likewise a nitinol wire. Alternatively, the transfer tube may includes coiled or braided polymer or plastic fibers reinforced with nitinol wire. The nickel titanium tube may be partitioned into concentric sections by end milling or radial laser cutting to define the concentric portions 158 and voids 156.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. A steerable surgical probe device comprising:
    an elongated, flexible transfer tube adapted for insertion into a surgical region, the transfer tube having a distal end and a proximate end, the proximate end attached to a control module;
    a lumen defined by an interior of the transfer tube;
    a laser fiber extending through the lumen and adapted for delivering a therapeutic laser signal to a treatment probe defined by a distal end of the laser fiber emanating from the distal end of the transfer tube;
    an articulating tip at the distal end of the transfer tube, the articulating tip responsive to articulating forces from a retractable tether for directing the treatment probe in a direction of the articulation;
    a linkage to the tether from the control module for effecting controlled retraction of the tether for articulating the tip towards a surgical target, the articulating tip imposing a bend radius on the laser fiber; and
    a detection circuit in the control module for identifying a signal loss through the laser fiber based on the bend radius imposed during articulation, further comprising an advancement control in the control module, the advancement control including:
    a rotating advancement knob;
    a threaded rod attached to the rotating advancement knob; and
    an actuation plate having a threaded receptacle, the threaded rod extending through the threaded receptacle, the threaded receptacle responsive for advancement based on rotation of the threaded rod; and
    a linkage between the actuation plate and the transfer tube for disposing the transfer tube.

2. The device of claim 1, wherein the articulating tip has at least one notched void defining opposed concentric sides, the opposed concentric sides adapted to dispose towards each other and close the void in response to tethered retraction.

3. The device of claim 2, further comprising an articulation actuator attached to the retractable tether, the retractable tether coupled to the distal end of the transfer tube on a distal side of the notched void, the tether adapted to draw the opposed concentric sides into proximity for inducing a deformable flexure in an unbroken circumference of the transfer tube.

4. The device of claim 2, wherein the articulating tip is formed from a nickel titanium tube having concentric notched sections partially removed to form an attachment between the sections.

5. The device of claim 4, wherein the partially removed concentric sections form a substantially linear spine of continuous material parallel to an axis of the nickel titanium tube.

6. The device of claim 4, wherein the nickel titanium tube forming the tip is welded to the transfer tube and the retractable tether includes nitinol.

7. The device of claim 4, wherein the retractable tether is a nitinol wire welded to the articulating tip.

8. The device of claim 1, wherein the articulating tip has an angle of articulation defined by a deviation from a nominal axis of the lumen, the angle of articulation resulting in the bend radius and a maximum angle of articulation is based on a signal strength of a laser signal emanating from the treatment probe following a passage through an articulated fiber portion at the bend radius.

9. The device of claim 1, further comprising a rotary steering control in the control module, the rotary steering control including:
    a rotating steering knob;
    a rotary linkage between the steering knob and the transfer tube, the rotary linkage providing circumferential rotation of the transfer tube for disposing the tip in an arcuate path based on the articulation.

10. The device of claim 1, further comprising a control linkage between the transfer tube and the control module, the control module further comprising:
    a steering control operable to rotate the transfer tube for transferring an axial rotation to the articulating tip;
    an advancement control for advancing the transfer tube relative to the control module for disposing the distal end relative to the control module; and
    a retraction control for drawing the retractable tether in a direction towards the control module and articulating the tip.

11. The device of claim 10, wherein the retraction control allows bidirectional movement of the retractable tether by disposing the retractable tether in a direction towards and away from the control module for varying an angle of articulation of the tip.

12. The device of claim 11, further comprising:
    a rotary encoder engaged with the steering control and configured to transmit a signal indicative of rotation of the transfer tube.

13. The device of claim 1, further comprising a rotary encoder engaged with the advancement control and configured to transmit a signal indicative of advancement of the transfer tube based on rotation of the threaded member.

14. The device of claim 1, wherein the detection circuit is further configured to:
    compare the identified signal loss to a threshold, the threshold indicative of a signal falling below a minimal therapeutic effectiveness; and
    rendering an indication of excessive signal degradation.

15. The device of claim 1, wherein the transfer tube is adapted for a passage through a working channel of an endoscopic surgical instrument.

16. The device of claim 1, further comprising:
    a flexible endoscope having a working channel, the working channel receptive to the transfer tube for a passage therethrough;
    the flexible endoscope having a therapeutic end for accessing a surgical site, the articulating tip extending beyond the therapeutic end for access to the surgical site;
    the flexible endoscope further comprising a camera channel for visual image transmission and at least one illumination source at the therapeutic end for illuminating the surgical site.

17. The device of claim 16, wherein the flexible endoscope has a diameter of 5 mm or less, the working channel has a diameter of 2 mm or less, and the transfer tube has a diameter of 1.8 mm or less.

\* \* \* \* \*